United States Patent
Borgmann

(10) Patent No.: US 7,745,655 B1
(45) Date of Patent: Jun. 29, 2010

(54) METHOD FOR THE PREPARATION OF BIPHOSPHITES

(75) Inventor: Cornelia Borgmann, Recklinghausen (DE)

(73) Assignee: Oxeno Olefinchemie GmbH, Marl (DE)

(*) Notice: Subject to any disclaimer, the term of this patent is extended or adjusted under 35 U.S.C. 154(b) by 1699 days.

(21) Appl. No.: 10/505,879

(22) PCT Filed: Nov. 28, 2002

(86) PCT No.: PCT/EP02/13418

§ 371 (c)(1),
(2), (4) Date: Sep. 3, 2004

(87) PCT Pub. No.: WO03/076448

PCT Pub. Date: Sep. 18, 2003

(30) Foreign Application Priority Data

Mar. 13, 2002 (DE) ................. 102 10 918

(51) Int. Cl.
*C07F 9/08* (2006.01)

(52) U.S. Cl. ...................................... 558/78

(58) Field of Classification Search .............. 546/22; 548/413; 556/13; 558/77, 78, 79
See application file for complete search history.

(56) References Cited

U.S. PATENT DOCUMENTS

| | | | |
|---|---|---|---|
| 5,093,534 A | 3/1992 | Ludwig et al. | |
| 6,331,657 B1 | 12/2001 | Kaizik et al. | |
| 6,403,837 B1 | 6/2002 | Hess et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Röttger et al. | |
| 6,818,770 B2 | 11/2004 | Selent et al. | |
| 6,924,389 B2 | 8/2005 | Jackstell et al. | |
| 6,956,133 B2 | 10/2005 | Jackstell et al. | |
| 7,109,346 B2 | 9/2006 | Beller et al. | |
| 2002/0111487 A1* | 8/2002 | Roettger et al. | ............... 546/22 |
| 2003/0144559 A1 | 7/2003 | Hess et al. | |
| 2003/0195368 A1 | 10/2003 | Rottger et al. | |
| 2005/0171371 A1 | 8/2005 | Borner et al. | |
| 2005/0209455 A1 | 9/2005 | Boerner et al. | |
| 2005/0209489 A1 | 9/2005 | Moller et al. | |
| 2005/0234270 A1 | 10/2005 | Kaizik et al. | |
| 2006/0089469 A1 | 4/2006 | Komarov et al. | |
| 2007/0149781 A1 | 6/2007 | Riermeier et al. | |
| 2007/0197799 A1 | 8/2007 | Holz et al. | |

FOREIGN PATENT DOCUMENTS

| | | |
|---|---|---|
| EP | 1 201 675 | 5/2002 |
| GB | 1 107 220 | 3/1968 |
| WO | 99 06416 | 2/1999 |

OTHER PUBLICATIONS

U.S. Appl. No. 12/065,091, filed Feb. 28, 2008, Hess et al.
U.S. Appl. No. 10/584,492, filed Jun. 22, 2006, Ortmann et al.
U.S. Appl. No. 10/525,376, filed May 8, 2006, Moeller et al.
U.S. Appl. No. 10/593,330, filed Sep. 19, 2006, Borgmann et al.
U.S. Appl. No. 09/708,646, filed Nov. 9, 2000, Hess et al.
U.S. Appl. No. 10/584,148, filed Jun. 22, 2006, Ortmann et al.
U.S. Appl. No. 11/908,343, filed Sep. 11, 2007, Holz et al.
Selent, D. et al. "New Phosphorus Ligands for the Rhodium-Catalyzed Isomerization/Hydroformylation of Internal Octenes", Angewandte Chemie International Edition. vol. 40, No. 9, pp. 1696-1698, XP002234378, ISSN: 0570-0833 2001.
U.S. Appl. No. 10/485,817, filed Jun. 15, 2004, Schmutzler et al.
U.S. Appl. No. 10/485,811, filed Feb. 10, 2004, Selent et al.
U.S. Appl. No. 10/911,499, filed Aug. 5, 2004, Selent et al.

* cited by examiner

*Primary Examiner*—Kamal A Saeed
*Assistant Examiner*—Kristin Bianchi
(74) *Attorney, Agent, or Firm*—Oblon, Spivak, McClelland, Maier & Neustadt, L.L.P.

(57) ABSTRACT

The present invention relates to a process for preparing bisphosphites which contain dioxaphosphorinone units.

8 Claims, No Drawings

METHOD FOR THE PREPARATION OF BIPHOSPHITES

The present invention relates to an improved process for the preparation of bisphosphites containing dioxaphosphorinone units.

Phosphites are widely used in a variety of different fields. Particularly important industrial uses are as antioxidants, as heat stabilizers in polymers such as PVC (=polyvinyl chloride) and in particular as ligands for transition metal catalysts.

A review of important homogeneous catalysts comprising phosphite ligands may be found, for example, in B. Cornils, W. A. Herrmann, Applied Homogeneous Catalysis with Organometallic Compounds Vol. 1 & 2, VCH, Weinheim, 1996, pages 29-187, 465-486.

Among homogeneously catalyzed reactions, hydrocyanation and especially carbonylation reactions such as hydroformylation are substantially influenced by phosphite ligands. A summary of rhodium-catalyzed hydroformylations using phosphite ligands is given in P. W. N. M. van Leeuwen, C. Clayer, Catalysis by Metal Complexes, Vol. 22 Rhodium Catalyzed Hydroformylation, Kluwer Academic Publishers, Dordrecht, 2000, pages 35-62, 107-130, 145-188, 233-252, 253-280.

Within the group of phosphites, chelating phosphites, in particular bisphosphites, are of particular importance as ligands for metal complexes. This is due to the fact that bisphosphites form more stable complexes with the respective central metal atom and thus have a more lasting effect on its catalytic properties.

DE 100 53 272.1 describes bisphosphites comprising dioxaphosphorinone units. In the synthesis described there, hydroxy compounds are reacted with phosphorus trichloride in the presence of the strong base butyllithium. Since the ability of butyllithium to ignite spontaneously in air poses a potential hazard, its handling requires specific and costly measures.

In BE 667 036 (Farbwerke Hoechst AG, 1966), the building block 2-chloro-1,3-dioxa-2-phosphaanthracen-4-one is obtained by reaction of 2-hydroxynaphthalene-1-carboxylic acid with phosphorus trichloride. The hydrogen chloride gas formed is driven out of the reaction mixture by heating under reflux. In a second variant, the disodium salt is firstly obtained from 2-hydroxynaphthalene-1-carboxylic acid by addition of aqueous sodium hydroxide, the water is subsequently removed by azeotropic distillation and the disodium salt is finally reacted with phosphorus trichloride. The disadvantages of this process are, firstly, production of the corrosive gas hydrogen chloride and, secondly, the complicated removal of water.

The use of phosphites in industrial processes, e.g. as ligand in the metal-catalyzed hydroformylation of olefins, makes it necessary for these compounds likewise to be produced in industrial quantities.

There is therefore a need to improve the known syntheses of bisphosphites containing dioxaphosphorinone units so that they can be carried out safely and more simply and are suitable for an industrial process.

The present invention accordingly provides a process for preparing bisphosphites of the formula I:

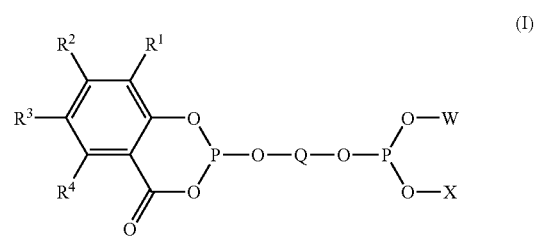

where $R^1$, $R^2$, $R^3$, $R^4$ are each H or an aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, F, Cl, Br, I, —$CF_3$, —$COR^7$, —$CO_2R^7$, —$CO_2M$, —$SR_7$, —$SO_2R^7$, —$SOR^7$, —$SO_3R^7$, —$SO_3M$, —$SO_2NR^7R^8$, $NR^7R^8$, N=$CR^7R^8$, $NH_2$, where $R^1$ to $R^4$ are identical or different and may be covalently linked to one another, $R^7$, $R^8$ are each H or a substituted or unsubstituted, aliphatic or aromatic hydrocarbon radical having from 1 to 25 carbon atoms and are identical or different, M is an alkali metal ion, alkaline earth metal ion, ammonium ion, phosphonium ion, Q is a divalent aliphatic, alicyclic, aliphatic-alicyclic, heterocyclic, aliphatic-heterocyclic, aromatic, aliphatic-aromatic hydrocarbon radical having from 1 to 50 carbon atoms, Z, Y are each Cl, Br, I, W, X are each an aliphatic, alicyclic, aliphatic-alicyclic, heterocylic, aliphatic-heterocyclic, aromatic, aromatic-aromatic, aliphatic-aromatic hydrocarbon radical having from 1 to 50 carbon atoms and may be identical or different or be covalently linked to one another, which comprises carrying out the reaction sequence

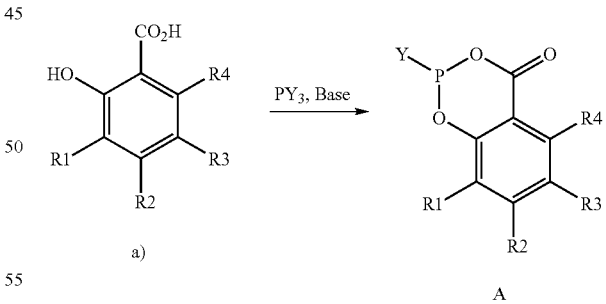

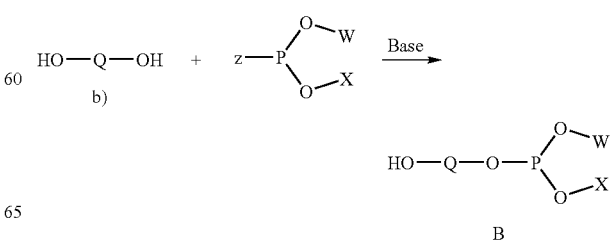

c) 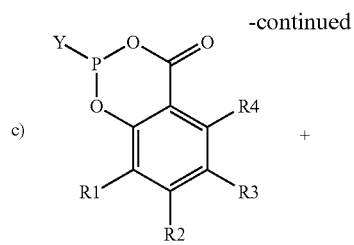

A

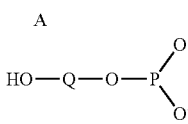 → Base

B

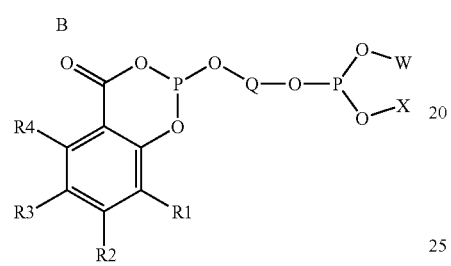

C where the reaction steps a), b) and c) are carried out in aprotic and nonpolar solvents.

A work-up of the products after the reaction steps a)-d) is not necessary; it is sufficient to filter off the precipitated solids (acid-base adduct) and to use the mixture obtained in this way without further purification in the next reaction step. The process of the invention can therefore be carried out batchwise or continuously, e.g. in a cascade of stirred vessels with appropriate filtration facilities.

The hydrogen halide-base products are insoluble in the aprotic solvents used, e.g. toluene, and are obtained as solids or, in the ideal case, precipitate from the solution.

The aprotic solvent should be chosen so that apart from the acid-base adduct, all products and starting materials are soluble in the solvent. However, it is possible for the intermediates A and/or B to be only sparingly soluble; however, these intermediates are converted during the course of the reaction into a preferred readily soluble end product.

The advantage of this procedure is that the insoluble hydrogen halide-base product can be removed from the reaction mixture by simple filtration, with the intermediate-containing filtrate being able to be used unchanged without isolation for the next step. In the simplest case, only the end product from the process has to be isolated and purified. Since the steps of isolation and purification require a longer period of time than the actual reaction, time and thus money can be saved when this procedure is employed.

Bases used in the process of the invention are preferably tertiary amines such as tri-n-propylamine, diisopropylisobutylamine, N-cyclohexyldimethylamine, N-methylmorpholine, N-methylpiperidine, N-methyl-pyrrolidine, N,N,N,N-tetramethylethylenediamine, DBU (1,8-diazabicyclo[5.4.0]undec-7-ene), DBN (1,5-diaza-bicyclo[4.3.9]non-5-ene), preferably triethylamine.

Preferred solvents are benzene, toluene, ethylbenzene, xylene, cyclohexane.

The process of the invention also encompasses the preparation of compounds in which two of the radicals $R^1$ to $R^4$ in the formula I are benzo-fused, i.e. $R^1$ and $R^2$, $R^2$ and $R^3$ or $R^3$ and $R^4$ can be linked to one another via an aromatic ring. This makes three isomers possible, and these can be used separately or together as ligand systems. The bisphosphites of the formula I prepared according to the invention can therefore also be compounds of the formulae II, III and IV.

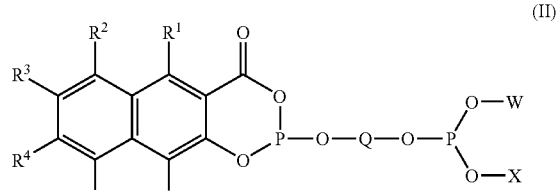 (II)

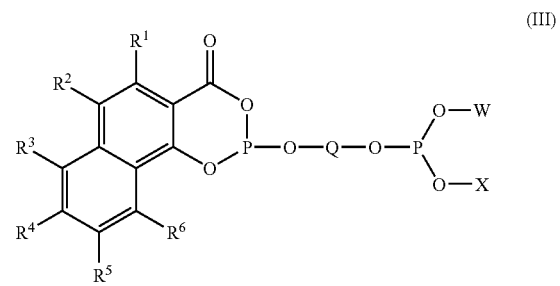 (III)

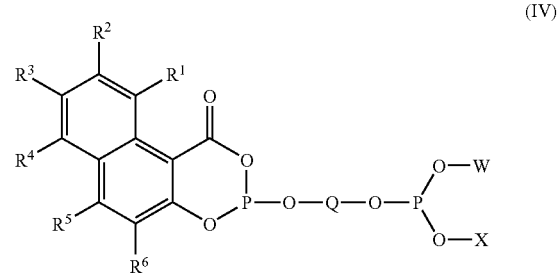 (IV)

The meanings of the radicals $R^1$ to $R^6$ correspond to the meanings of $R^1$ to $R^4$ defined for formula I. It is possible for these radicals likewise to be covalently linked to one another or to be benzo-fused.

The process of the invention can also be used to prepare bisphosphites of the formulae V, VI and VII.

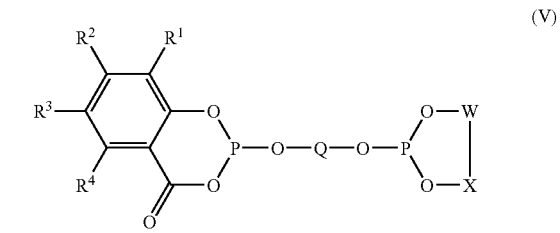 (V)

-continued

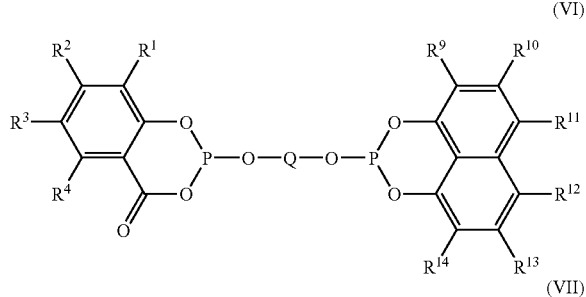

(VI)

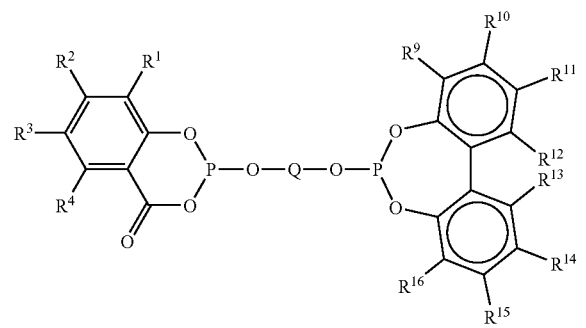

(VII)

In these formulae, W and X are aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, X and W may be identical or different or be covalently linked to one another and $R^1$, $R^2$, $R^3$, $R^4$, $R^5$, $R^6$, $R^7$, $R^8$ and Q are as defined above.

$R^9$, $R^{10}$, $R^{12}$, $R^{13}$, $R^{14}$, $R^{15}$, $R^{16}$ are each H or an aliphatic, alicyclic, aliphatic-alicyclic, hetero-cyclic, aliphatic-heterocyclic, aromatic, aromatic-aromatic, aliphatic-aromatic hydrocarbon radicals having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, N=$CR^{25}R^{26}$, $NH_2$, where $R^9$ to $R^{16}$ are identical or different and may be covalently linked to one another.

M is an alkali metal ion, alkaline earth metal ion, ammonium ion or phosphonium ion.

$R^{25}$ and $R^{26}$ can be identical or different and are each H or a substituted or unsubstituted, aliphatic or aromatic hydrocarbon radical having from 1 to 25 carbon atoms.

Examples of Q are bivalent hydrocarbon radicals which may be aliphatic, alicyclic, aliphatic-alicyclic, heterocyclic, aliphatic-heterocyclic, aromatic, aromatic-aromatic or aliphatic-aromatic. Any ring systems present can in turn be substituted by the abovementioned hydrocarbon radicals. In open-chain structural elements, one or more methylene groups may be replaced by oxygen and/or sulfur and/or $NR^1$ and/or NH and/or one or more CH groups may be replaced by nitrogen.

Q is preferably a bivalent radical containing aromatic groups. Q can be, for example, a phenylene radical, a naphthylene radical, a divalent bisarylene radical or a bivalent radical of a diphenyl ether. Furthermore, Q can have the general structure —Ar—V—Ar—. Here, Ar is a monocyclic or oligocyclic bivalent aromatic radical. V is either a direct bond or a substituted or unsubstituted methylene group —$CR^{27}R^{28}$— where $R^{27}$ and $R^{28}$ are each hydrogen or an aliphatic or aromatic radical having from 1 to 25 carbon atoms which may additionally contain heteroatoms. Furthermore, the radicals $R^{27}$ and $R^{28}$ may be joined to form one or more rings, i.e. have a covalent bond.

Among the bisphosphites of the formulae I, II, III, IV, V, VI and VII, particular preference is given to those in which the radical Q is a hydrocarbon radical (bisarylene radical) of the formula VIII

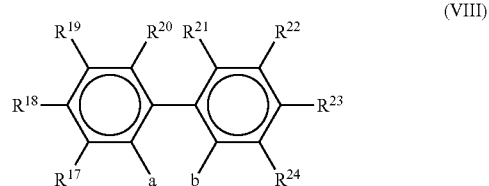

(VIII)

where $R^{17}$, $R^{18}$, $R^{19}$, $R^{20}$, $R^{21}$, $R^{22}$, $R^{23}$, $R^{24}$ are each H or an aliphatic, alicyclic, aliphatic-alicyclic, heterocyclic, aliphatic-heterocyclic, aromatic-aromatic, aromatic, aliphatic-aromatic hydrocarbon radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SOR^{25}$, —$SO_3R^{25}$, —$SO_3R^{25}$, —$SO_3M$, —$SO_2NR^{25}R^{26}$, $NR^{25}R^{26}$, N=$CR^{25}R^{26}$, $NH_2$, where $R^{17}$ to $R^{24}$ are identical or different and may be covalently linked to one another, $R^{25}$, $R^{26}$ are each H or a substituted or unsubstituted, aliphatic or aromatic hydrocarbon radical having from 1 to 25 carbon atoms, M is an alkali metal ion, alkaline earth metal ion, ammonium ion, phosphonium ion, where the positions a and b are the linkage points of the substituent in the structural element O-Q-O in the compounds of the formula I to VII.

The following reaction sequence illustrates the process of the invention using the compound VII as an example:

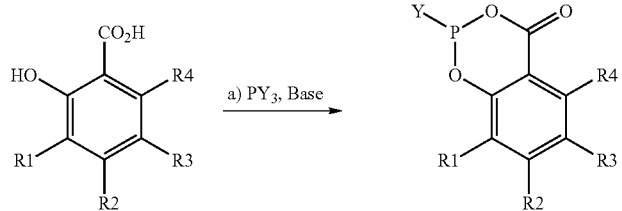

A

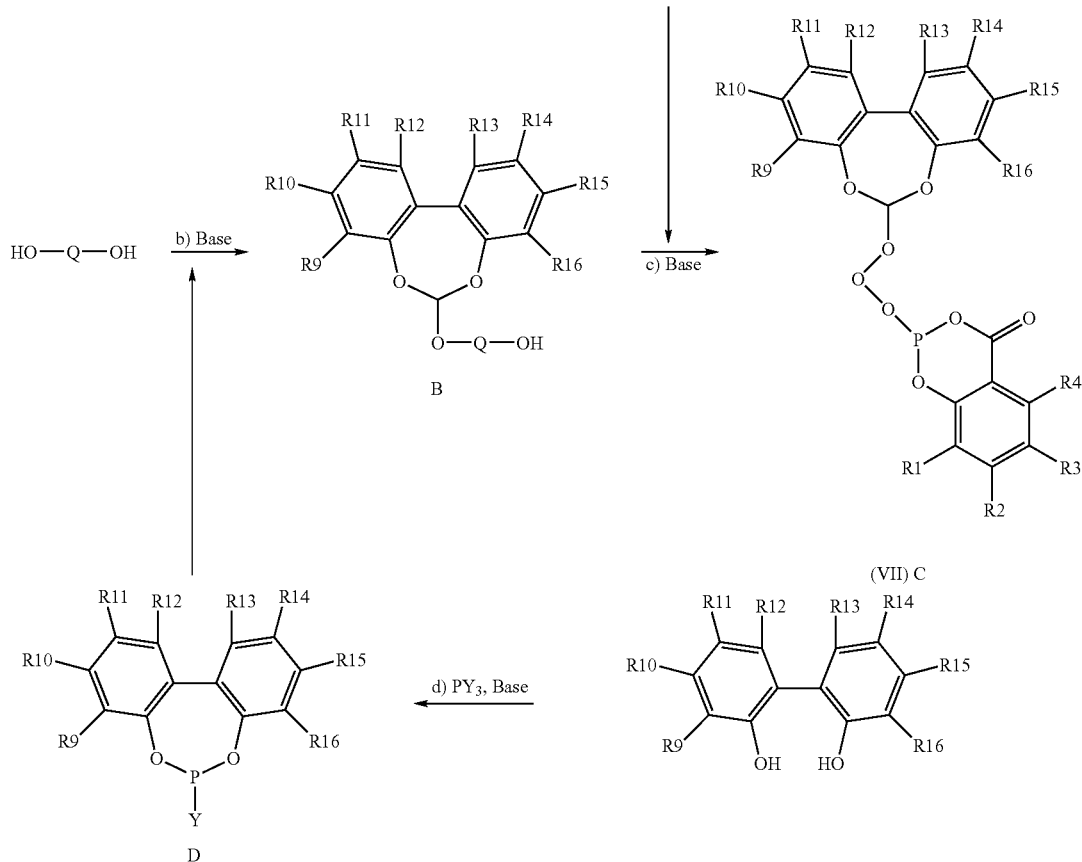

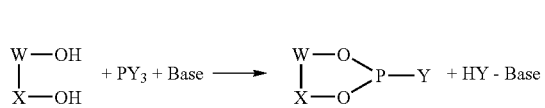

where $R^1$ to $R^4$ and $R^9$ to $R^{16}$ are as defined above, $PY_3$ can be phosphorus trichloride, phosphorus tribromide or phosphorus triiodide and the base is in each case a tertiary amine such as triethylamine.

In a particular embodiment of the invention, W and X are covalently linked and the corresponding starting material used in reaction step c) is prepared according to reaction step d) using an aprotic and nonpolar solvent as described by the following scheme d).

As an alternative to this route, it is possible for the intermediate A firstly to react with the diol HO-Q-OH and the intermediate B to be subsequently introduced.

The solvents used in the process of the invention are, of course, inert toward the reactants. They have to be selected so that, firstly, they dissolve the reactants sufficiently well and, secondly, they do not dissolve the hydrogen halide product, so that this by-product precipitates during the reaction. These requirements are met by aprotic and nonpolar solvents such as toluene.

The solvents used have to be largely free of water and oxygen; preference is given to solvents having a water content of 0-500 ppm, particularly preferably 0-250 ppm. The water content can, for example, be determined by the Karl Fischer method.

The solvent can be dried by distillation of the solvent over a suitable desiccant or by passing the solvent through a cartridge or column filled, for example, with 4 Å molecular sieves.

The process steps a), b), c) and d) are preferably carried out at temperatures of from −80° C. to 150° C.; in most cases, it has been found to be useful to work at temperatures of from −20° C. to 110° C., particularly preferably from 0° C. to 80° C.

The hydrogen halide-base adduct is removed from the reaction mixture by filtration after at least one, preferably after each, of the reaction steps a), b), c) and d).

In this filtration, solid constituents are separated from the solution by passage through a porous layer, viz. the filter medium, which is permeable to the solution and holds back the solid. Methods of filtration are summarized in C. Alt, Filtration, Ullmanns Enzyklopädie der technischen Chemie, 4th Edition, Verlag Chemie, Weinheim, 1972, Vol. B2, Chapters 9 and 10.

To monitor the process steps a), b), c) and d), it is possible to employ general analytical methods such as mass spectroscopy (MS), gas chromatography either coupled with mass spectroscopy or on its own (GC/MS or GC), liquid chromatography either coupled with mass spectroscopy or on its own (LC/MS or MS [sic]) or nuclear magnetic resonance spectroscopy (NMR).

The process steps a), b), c) and d) are carried out under protective gas such as nitrogen or argon because of the oxidation sensitivity of the reactants.

The process steps d) and b) can be carried out without interruption in a single-vessel process, so that the number of process steps can be minimized.

EXAMPLES

The following examples were carried out with the aid of standard Schlenk techniques, although the synthesis can also be carried out on a kg scale.

Example 1

Preparation of compound 1

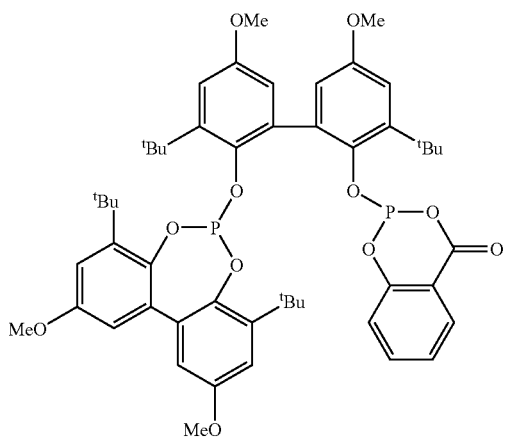

1

Process Step a)

In a 500 ml Schlenk tube, 23.4 g (0.17 mol) of salicylic acid are admixed with 170 ml of toluene. 50 ml of toluene, 71.0 ml (51.6 g; 0.51 mol) of triethylamine and 14.8 ml (23.3 g; 0.17 mol) of phosphorus trichloride are introduced in succession into a 500 ml Schlenk tube while stirring. This solution is added dropwise to the salicylic acid/toluene mixture over a period of 40 minutes while stirring at 0-4° C. After the addition is complete, the mixture is warmed to room temperature over a period of 2 hours and is subsequently stirred for another 2 hours at room temperature. During this time, the triethylammonium chloride formed precipitates as a white solid and is separated off via a frit. The filtrate is analyzed by GC/MS and stored until it is reacted further in process step c).

Process Step d)

35.8 g (0.1 mol) of 3,3'-tert-butyl-2,2'-dihydroxy-5,5'-dimethoxybiphenyl are admixed with 180 ml of toluene and 46 ml (=33.4 g; 0.33 mol) of triethylamine and dissolved with stirring. This solution is added dropwise to a solution of 8.77 ml (=13.8 g; 0.1 mol) of phosphorus trichloride in 80 ml of toluene over a period of 1 hour 30 minutes at a temperature of 0-4° C. while stirring. After the addition is complete, the mixture is warmed to room temperature over a period of 2 hours and is subsequently stirred for another 2 hours at room temperature. During this time, the triethylammonium chloride formed precipitates as a white solid. This is separated off with the aid of a frit, the filtrate is analyzed by GC/MS and stored until it is reacted further in process step c).

Process Step b)

In a 1 l Schlenk tube, 35.8 g (0.1 mol) of 3,3'-tert-butyl-2,2'-dihydroxy-5,5'-dimethoxybiphenyl are dissolved in 300 ml of toluene and 13.9 ml (=10.12 g; 0.1 mol) of triethylamine while stirring. The solution prepared in process step b), which contains the intermediate D, is added dropwise at room temperature to the above solution over a period of 2 hours. After the addition is complete, the mixture is stirred at room temperature for another 30 minutes, with triethylammonium chloride precipitating as a white solid. To check for complete conversion, the solution of the reaction mixture is analyzed by means of LC/MS. If the starting compounds have not reacted completely, the reaction mixture is heated at 80° C. for 2 hours. After cooling to room temperature, the triethylammonium chloride which has precipitated is filtered off via a frit and the filtrate is stored for further processing in process step c).

Process Step c)

15.9 ml (=11.57 g; 0.11 mol) of triethylamine are added to the filtrate from process step b), which contains the intermediate B. The filtrate from process step a), which contains the intermediate A, is added dropwise to this solution at 0° C. over a period of 2.5 hours. The reaction mixture is subsequently warmed to room temperature and stirred at room temperature for another 2 hours. For the work-up, the precipitated triethylammonium chloride is filtered off via a frit. After the solvent has been distilled off from the filtrate in an oil pump vacuum, the residue is slurried in 400 ml of acetonitrile, the product is filtered off via a frit, the residue is washed twice with 50 ml of acetonitrile and finally dried in an oil pump vacuum.

Total yield: 40-60% (based on the biphenyl compound)

Purity ($^{31}$P-NMR): >99%

$^{31}$P-NMR (CD$_2$Cl$_2$): δ 119.2 (m); 119.8 (m); 139.5 (m); 140.1 (m);

$^1$H NMR (CD$_2$Cl$_2$) 1.02 ... 1.26 (36H); 3.67 ... 3.74 (12H); 6.43 ... 7.99 (12H);

FAB-MS: m/e 911 (100%, M+), 744 (18%), 387 (13%).

Example 2

Process Steps a) and c) as in Example 1

Process Steps d) and b):

In a 1 l Schlenk tube, 71.6 g (0.2 mol) of 3,3-tert-butyl-2,2'-dihydroxy-5,5,-dimethoxybisphenol are dissolved in 450 ml of toluene and 59.9 ml (0.43 mol) of triethylamine while stirring. Half of this solution is added dropwise while stirring at −20° C. to a solution of 8.77 ml (0.1 mol) of phosphorus trichloride in 80 ml of toluene over a period of 1 hour 30 minutes. After the addition is complete, the mixture is warmed to 0-4° C. over a period of 2 hours and is stirred for another 2 hours. The second half of the bisphenyl/triethylamine solution is added to the above solution at 0-4° C. over a period of 1 hour 30 minutes. The reaction mixture is warmed to room temperature and stirred for another 2 hours. To check for complete conversion, the solution of the reaction mixture is analyzed by means of LC/MS.

If the starting compounds have not yet reacted completely, the reaction mixture is heated at 80° C. for 2 hours. After cooling to room temperature, the triethylammonium chloride which has precipitated is filtered off via a frit and the filtrate is stored for further processing Process step d).

The invention claimed is:

1. A process for preparing bisphosphites of the formula I

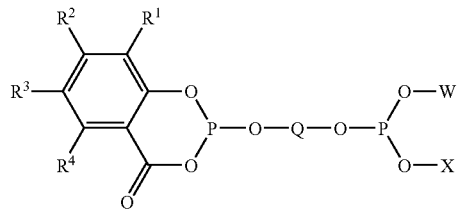

wherein $R^1$, $R^2$, $R^3$, $R^4$ are independently selected from H, aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, F, Cl, Br, I, —$CF_3$, —$OR^7$, —$COR^7$, —$CO_2R^7$, —$CO_2M$, —$SR_7$, —$SO_2R^7$, —$SOR^7$, —$SO_3R^7$, —$SO_3M$, —$SO_2NR^7R^8$, $NR^7R^8$, $N{=}CR^7R^8$, or $NH_2$, wherein $R^1$ to $R^4$ may be covalently linked to one another, $R^7$, $R^8$ are independently selected from H or a substituted or unsubstituted, aliphatic or aromatic hydrocarbon radical having from 1 to 25 carbon atoms, atoms, M is an alkali metal ion, alkaline earth metal ion, ammonium ion, or phosphonium ion, Q is a divalent aliphatic, alicyclic, aliphatic-alicyclic, heterocyclic, aliphatic-heterocyclic, aromatic, or aliphatic-aromatic hydrocarbon radical having from 1 to 50 carbon atoms, Z, Y are each Cl, Br, or I, W, X are independently selected from an aliphatic, alicyclic, aliphatic-alicyclic, heterocyclic, aliphatic-heterocyclic, aromatic, aromatic-aromatic, or aliphatic-aromatic hydrocarbon radical having from 1 to 50 carbon atoms and may be covalently linked to one another, the process comprising carrying out the reaction sequence a)

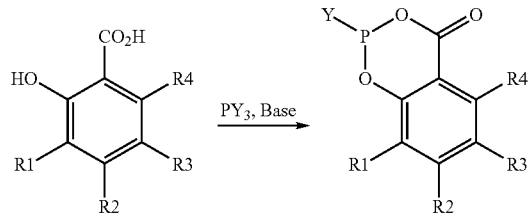

b)

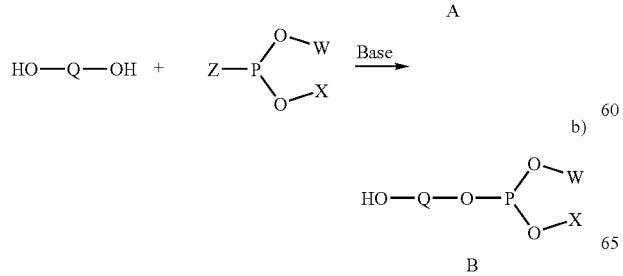

c)

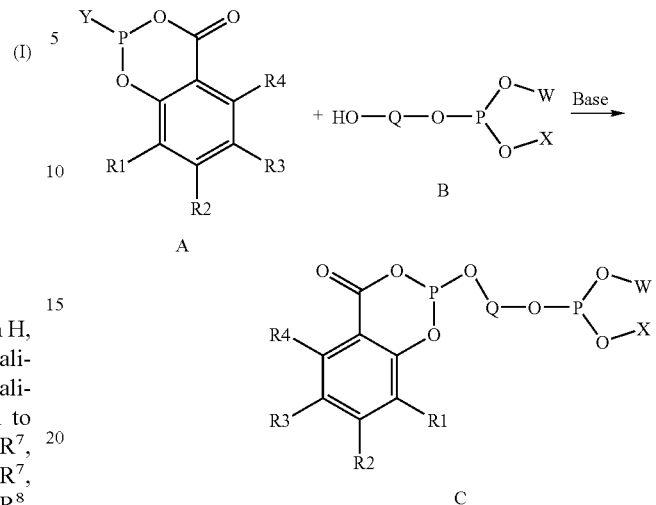

wherein the reaction steps a), b) and c) are carried out in aprotic and nonpolar solvents, the adduct base•HY or base•HZ is filtered off after at least one of the reaction steps a), b) and c) and the end product is isolated and purified.

2. The process as claimed in claim 1, wherein said base comprises tertiary amines.

3. The process as claimed in claim 1, wherein said aprotic and nonpolar solvents are at least one selected from the group consisting of benzene, toluene, ethylbenzene, and cyclohexane.

4. The process as claimed in claim 1, wherein W and X are an independently selected from aliphatic, alicyclic, aliphaticalicyclic, heterocyclic, aliphatic-heterocyclic, aromatic, aromatic-aromatic, or aliphatic-aromatic hydrocarbon radical having from 1 to 50 carbon atoms and are covalently linked as in the formula V

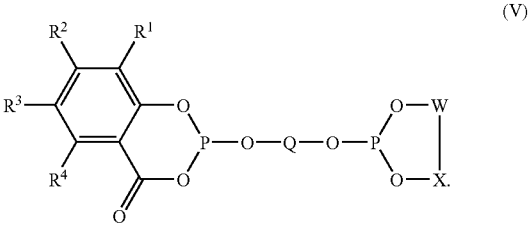

5. The process as claimed in claim 1, wherein W and X are each an aromatic hydrocarbon radical having from 1 to 50 carbon atoms and are covalently linked as shown in the formula VI

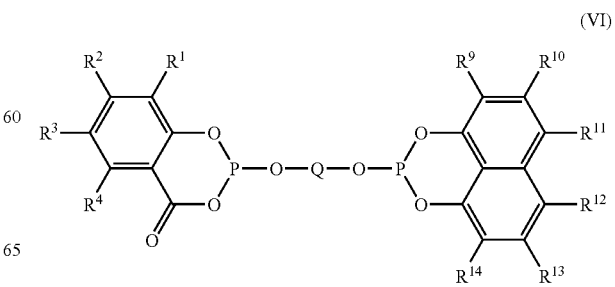

wherein $R^9$, $R^{10}$, $R^{11}$, $R^{12}$, $R^{13}$, $R^{14}$ are independently selected from H aliphatic, alicyclic, aliphatic-alicyclic, heterocyclic, aliphatic-heterocyclic, aromatic-aromatic, aromatic, aliphatic-aromatic hydrocarbon radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, or $NH_2$, wherein $R^9$ to $R^{14}$ may be covalently linked to one another;

$R^{25}$ and $R^{26}$ are independently selected from H or a substituted or unsubstituted, aliphatic or aromatic hydrocarbon radical having from 1 to 25 carbon atoms, and M is an alkali metal ion, alkaline earth metal ion, ammonium ion, or phosphonium ion.

6. The process as claimed in claim 1, wherein W and X are each an aromatic hydrocarbon radical having from 1 to 50 carbon atoms and are covalently linked as shown in the formula VII

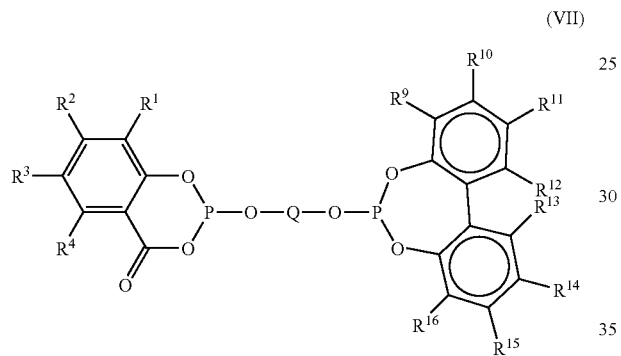

(VII)

wherein $R^9$, $R^{10}$, $R^{11}$, $R^{12}$, $R^{13}$, $R^{14}$, $R^{15}$, $R^{16}$ are independently selected from H, aliphatic, alicyclic, aliphatic-alicyclic, heterocyclic, aliphatic-heterocyclic, aromatic-aromatic, aromatic, aliphatic-aromatic hydrocarbon radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, or $NH_2$, wherein $R^9$ to $R^{16}$ may be covalently linked to one another, $R^{25}$ and $R^{26}$ are independently selected from H or a substituted or unsubstituted, aliphatic or aromatic hydrocarbon radical having from 1 to 25 carbon atoms, and M is an alkali metal ion, alkaline earth metal ion, ammonium ion, or phosphonium ion.

7. The process as claimed in claim 1, wherein Q is a hydrocarbon radical of the formula VIII

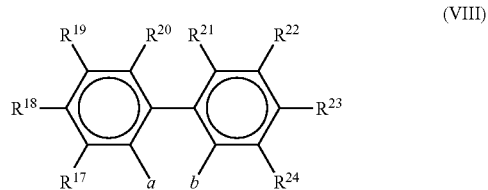

(VIII)

wherein $R^{17}$, $R^{18}$, $R^{19}$, $R^{20}$, $R^{21}$, $R^{22}$, $R^{23}$, $R^{24}$ are independently selected from H, aliphatic, alicyclic, aliphatic-alicyclic, heterocyclic, aliphatic-heterocyclic, aromatic-aromatic, aromatic, aliphatic-aromatic hydrocarbon radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, or $NH_2$, wherein $R^{17}$ to $R^{24}$ may be covalently linked to one another, $R^{25}$ and $R^{26}$ are independently selected from H or a substituted or unsubstituted, aliphatic or aromatic hydrocarbon radical having from 1 to 25 carbon atoms, and M is an alkali metal ion, alkaline earth metal ion, ammonium ion, or phosphonium ion with the positions a and b serving as linkage points.

8. The process as claimed in claim 1, wherein X and W are covalently linked and the corresponding starting material B used in reaction step c) is prepared according to reaction step d) in an aprotic and nonpolar solvent

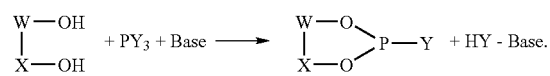

d)

* * * * *